United States Patent [19]

Terry, Jr. et al.

[11] Patent Number: 5,215,086
[45] Date of Patent: Jun. 1, 1993

[54] THERAPEUTIC TREATMENT OF MIGRAINE SYMPTOMS BY STIMULATION

[75] Inventors: Reese S. Terry, Jr., Houston; Joachim F. Wernicke, League City; Ross G. Baker, Jr., Houston, all of Tex.

[73] Assignee: Cyberonics, Inc., Webster, Tex.

[21] Appl. No.: 695,216

[22] Filed: May 3, 1991

[51] Int. Cl.⁵ .............................................. A61N 1/36
[52] U.S. Cl. .................................................... 128/421
[58] Field of Search ................ 128/419 C, 419 R, 421, 128/423 R, 732; 600/26

[56] References Cited

U.S. PATENT DOCUMENTS

| | | | |
|---|---|---|---|
| 3,908,634 | 9/1975 | Monaghan | 600/28 |
| 4,503,863 | 3/1985 | Katims | 128/421 |
| 4,509,521 | 4/1985 | Barry | 128/419 C |
| 4,537,195 | 8/1985 | McDonnell | 128/422 |
| 4,539,993 | 9/1985 | Stanton | 128/421 |
| 4,627,438 | 12/1986 | Liss et al. | 128/419 R |
| 4,856,526 | 8/1989 | Liss et al. | 128/422 |
| 4,867,164 | 9/1989 | Zabara | 128/421 |
| 5,067,495 | 11/1991 | Brehm | 128/421 |

FOREIGN PATENT DOCUMENTS

| | | | |
|---|---|---|---|
| 1194417 | 11/1965 | U.S.S.R. | 128/421 |
| 0591796 | 2/1978 | U.S.S.R. | 128/419 R |
| 1263256 | 10/1986 | U.S.S.R. | 128/421 |

Primary Examiner—William E. Kamm
Attorney, Agent, or Firm—Leitner, Greene & Christensen

[57] ABSTRACT

Method and apparatus for treating and controlling migraine by selectively applying a predetermined electrical signal to the patient's vagus nerve for stimulation thereof to alleviate the migraine attack. The signal is a pulse waveform having parameters programmed to desynchronize the patient's EEG if paroxysmal activity is detected in the EEG, or to synchronize the EEG if low voltage fast wave activity is detected. Alternatively, the application of the stimulating signal to the vagus nerve may be initiated manually by the patient upon recognition of the onset of a migraine attack. The neurostimulator device implanted in the patient to generate the appropriate signal has a power down circuit to conserve battery power between migraine episodes.

18 Claims, 2 Drawing Sheets

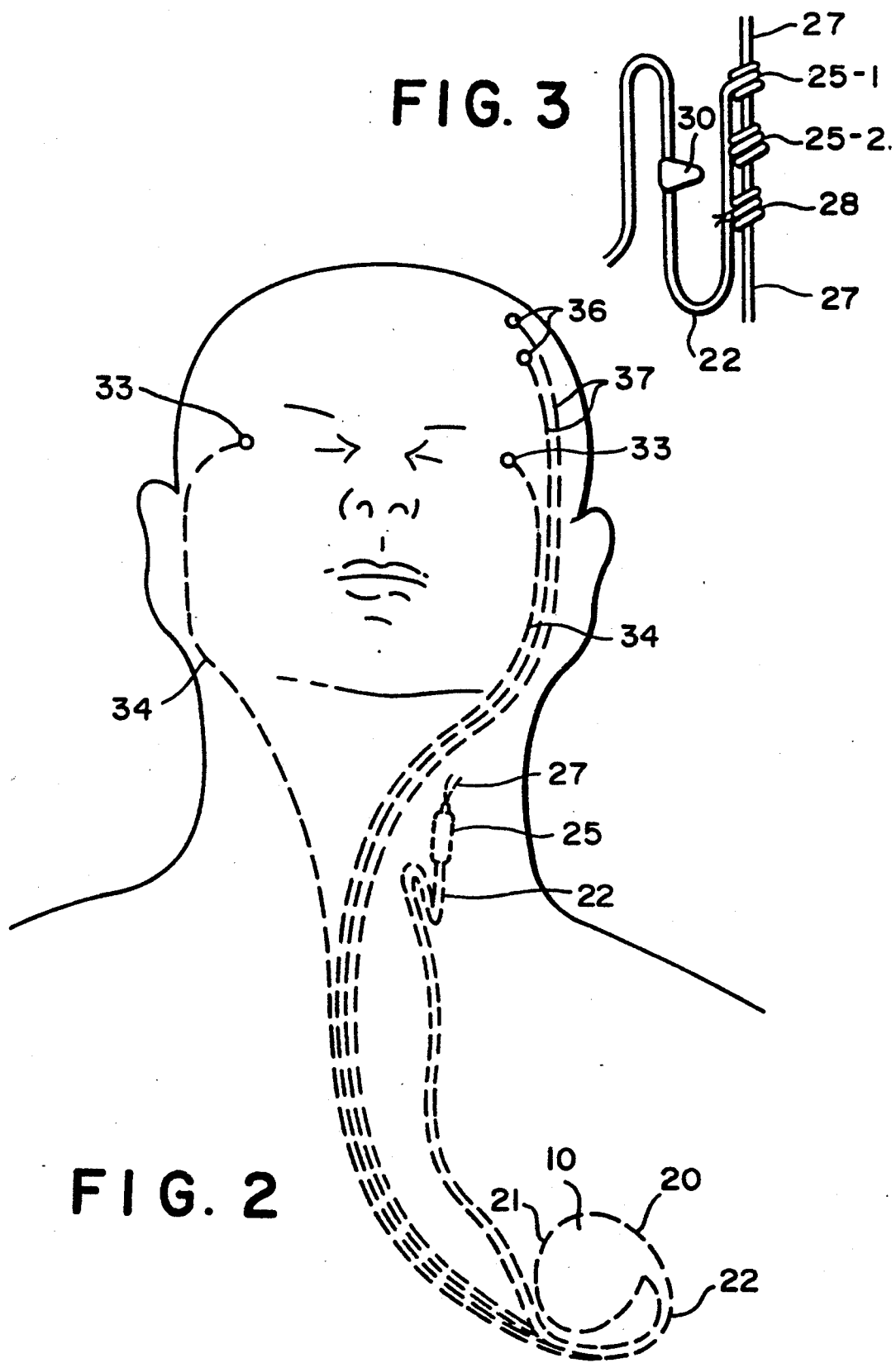

THERAPEUTIC TREATMENT OF MIGRAINE SYMPTOMS BY STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating patients with migraine by application of such signals to a cranial nerve, using an implantable neurostimulating device. Specifically, the invention is directed toward treating migraine by selective modulation of vagus nerve electrical activity.

Migraine is defined as a recurring vascular headache usually characterized by unilateral onset and severe pain, photophobia, and autonomic disturbances during the acute phase, which may last for hours or days. Classical migraines are associated with a prodromal aura; common migraines do not have a prodrome. The exact mechanism responsible for the disorder is not known, but the head pain is related to dilatation of extracranial blood vessels, which may be the result of chemical changes that cause spasms of intracranial vessels. The prodromes are thought to be related to constriction of the arterioles.

A relationship between migraine and epilepsy is indicated in the literature. See, for example, Basser, *Brain* (1969) 92:285-300; Hockaday et al., *Brain* (1969) 92:769-788. Although the two conditions are distinct, they have some areas of commonality. For one thing, patients with migraine are more likely to have epilepsy than those without migraine. For another, many patients with migraine have a strong family history of epilepsy. Other areas of commonality are that both migraine and epilepsy are paroxysmal and involve the brain in either a focal or spreading fashion, and both disorders may be associated with loss of consciousness as well as ictal or interictal EEG abnormalities. A neural disturbance, rather than vascular pathophysiology as the basis for migraine has been proposed by Gordon in *Dev. Med. Child. Neurol.* 31:682-689. Other reviews and references to specific studies and case reports are cited below.

In *Med. Clin. North Am.* (1978) 62:571-584, Masland reported finding that many patients with classic and common migraines demonstrate EEG paroxysms, which are seldom seen with cluster and tension headaches. Narbone et al., in *Headache* (1988) 28:209-211, describe one patient and refer to literature on others who have classical migraine, with seizures intercalated between the prodrome and cephalgia phase of the headache. Twomey et al. reported in *Acta Neurol. Scand.* (1988) 77:335-338 two cases in which status epilepticus may have immediately followed migraine, with one resulting in death.

The most important similarity between epilepsy and migraine may be and probably is paroxysmal EEG activity. It is unlikely that the cortical electrical activity is merely the result of altered blood flow associated with migraine, since this would probably result in slowing.

Ethical drugs, such as ergotamine and propranolol, have been the treatment of choice for migraine. However, we submit that migraine may share an underlying pathophysiology with epilepsy, and postulate that vagal stimulation can be effective for treating migraine.

In addressing a therapy involving nerve stimulation to treat migraine, observation should be made of existing knowledge that most nerves in the human body are composed of thousands of fibers, having different sizes designated by groups A, B and C, carrying signals to and from the brain and other parts of the body. The vagus nerve, for example, may have approximately 100,000 fibers (axons) of the three different types, each of which carries such signals. Each axon of that nerve only conducts in one direction, in normal circumstances. The A and B fibers are myelinated, that is, they have a myelin sheath in the form of a substance largely composed of fat. On the other hand, the C fibers are unmyelinated.

Myelinated fibers are typically larger, have faster electrical conduction and much lower electrical stimulation thresholds than the unmyelinated fibers. Along with the relatively small amounts of electrical energy needed to stimulate the myelinated fibers, it is noteworthy that such fibers exhibit a particular strength-duration curve in response to a specific width and amplitude of stimulation pulse.

The A and B fibers are stimulated with relatively narrow pulse widths, from 50 to 200 microseconds ($\mu s$), for example. A fibers exhibit slightly faster electrical conductivities than the B fibers, and slightly lower electrical stimulation thresholds. The C fibers are relatively much smaller, conduct electrical signals very slowly, and have high stimulation thresholds typically requiring wider pulse widths (e.g., 300-1000 $\mu s$) and higher amplitudes for activation. Although the A and B fibers may be selectively stimulated without also stimulating the C fibers, the magnitude and width of the pulse required for stimulating the C fibers would also activate A and B fibers.

Although electrical stimulation of the nerve fiber typically activates neural signals in both directions (bi-directionally), selective unidirectional stimulation is achievable through the use of special nerve electrodes and stimulating waveforms. As noted above, each axon of the vagus nerve normally conducts in only one direction.

In a paper on the effects of vagal stimulation on experimentally induced seizures in rats (*Epilepsia* (1990) 31 (Supp 2): S7-S19), Woodbury has noted that the vagus nerve is composed of somatic and visceral afferents (i.e., inward conducting nerve fibers which convey impulses toward a nerve center such as the brain or spinal cord) and efferents (i.e., outward conducting nerve fibers which convey impulses to an effector to stimulate it and produce activity). The vast majority of vagal nerve fibers are C fibers, and a majority are visceral afferents having cell bodies lying in masses or ganglia in the neck. The central projections terminate, by and large, in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

Woodbury further notes that stimulation of vagal nerve afferent fibers in animals evokes detectable changes of the EEG in all of these regions, and that the nature and extent of these EEG changes depends on the stimulation parameters. Chase, in *Exp Neurol* (1966) 16:36-49, had also observed that vagal activation can affect the EEG activity of certain parts of the brain.

The applicants herein postulate that synchronization of the EEG may be produced when high frequency (>70 Hz) weak stimuli activate only the myelinated (A and B) nerve fibers, and that desynchronization of the EEG occurs when intensity of the stimulus is increased to a level that activates the unmyelinated (C) nerve fibers. Woodbury also observes that vagal stimulation can produce widespread inhibitory effects on seizures and certain involuntary movements.

Extra-physiologic electrical stimulation of the vagus nerve has previously been proposed for treatment of epilepsy and various forms of involuntary movement disorders. Specifically, in U.S. Pat. No. 4,702,254 issued Oct. 27, 1987 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve in particular.

The NCP disclosed in the '254 patent may be activated either manually or automatically, to provide treatment for the duration of the seizure Manual activation is performed when the patient experiences the aura at onset of the seizure. Alternatively, automatic activation may be triggered upon detection of instantaneous changes in certain state parameters immediately preceding or at onset of a seizure. Additionally, a prophylactic or preventive mode may be employed in which the NCP is activated periodically to reduce the occurrence and/or the intensity of the seizures. The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

It is a principal object of the present invention to apply the techniques of selective modulation of vagus nerve electrical activity, using a neurostimulator device which may be implantable, or used external to the body with only a small portion of the circuitry implanted or with only the nerve electrode(s) and associated lead(s) implanted percutaneously in the body, to the treatment of migraine.

SUMMARY OF THE INVENTION

The present invention is directed to methods and devices for treating and controlling migraine by selective stimulation of the vagus nerve (the tenth cranial nerve) in a predetermined manner primarily to desynchronize the patient's EEG. In some instances, the treatment may be administered to synchronize the patient's EEG and/or to modify the patient's sleep patterns which are detected to be abnormal, depending on the particular patient.

The apparatus of the invention employs a neurostimulator (preferably but not necessarily implantable) to selectively apply a therapy to treat migraine. The therapy is delivered in a manner to modulate the electrical activity of the patient's vagus nerve in a predetermined manner to treat and relieve the effects of migraine, and the neurostimulator is programmed by the attending physician to provide the desired therapeutic modality for that purpose.

Selection among various strategies for vagal modulation to treat migraine depends on a number of factors. These include (i) a consideration of which of the nerve fibers are to be subjected to the modulation; (ii) the modality for achieving synchronization or desynchronization of the EEG; (iii) whether some type of physiologic signal is generated which can be detected and employed to trigger the modulation; and/or (iv) whether a "carryover" or refractory period occurs after modulation in which the benefit of the modulation is maintained. Although these are not all of the factors to be considered for selecting a stimulation strategy for treatment of the disorder, nor necessarily listed in order of importance, they are indicative of considerations which may apply in a specific case.

In the treatment, the invention uses different signal parameters and threshold curves to activate the various fibers of the patient's vagus nerve for selective modulation of the electrical activity thereof. By appropriately setting pulse width and amplitude of the electrical signal to be delivered by the neurostimulator to the patient's vagus nerve, the nerve fibers can be selectively stimulated, such as A and not B and C; or A and B, but not C; or A, B and C. Various related factors, however, must be considered in the selection process. For example, because the C fibers conduct signals very slowly, they are not highly responsive to techniques of fast stimulation. Therefore, if it were desired to increase desynchronous activity of the EEG by stimulation of the C fibers at 50 Hz, for example, for treatment of migraine in a particular patient, it would be prudent to use a short pulse train for the stimulus. This is because the fibers would become refractory to the stimulation within a relatively short time interval and thus incapable of tracking the pattern of a longer train. After a suitable recovery period, another short pulse train may be applied to achieve further treatment. The precise pattern to be used, e.g., the length of the time intervals on and off, will depend upon and be adjusted to the individual patient and the particular nature of the migraine being treated.

Furthermore, proper designation of amplitude and frequency range of the applied signals allows tuning of the fibers for the EEG desynchronization or synchronization, to control treatment of the migraine. Desynchronization of the EEG has been found to be achieved by stimulation at frequencies in the range from about 20 to about 75 Hz at levels above 0.1 volt, but requires signals greater than 3 volts at frequencies above 75 Hz. If the frequency is above 75 Hz and the signal is below 3 volts, EEG synchronization is achieved. The actual voltage required depends on the type and geometry of the electrode and the impedance of the electrode-tissue interface.

According to the invention, the basic stimulation strategy is to perform vagal modulation to desynchronize the EEG, or in some cases to synchronize it, depending on the particular patient. For patients who display paroxysmal activity, desynchronization will be the primary mode of therapy. Synchronization may be used for patients who display excessive low voltage, fast wave activity. In either case, the desire is to appropriately modulate the activity of a number of brain structures in the pathway for vagal activity, including the limbic system, the reticular formation, and the hippocampus. As described by Rutecki in *Epilepsia* (1990) 31 (Supp. 2): S1-S6, the vagus nerve projects directly or indirectly to these brain structures.

Preferably, this strategy is implemented primarily by patient activation of the neurostimulator upon his or her sensing the aura on onset of the attack in the case of classical migraine, or the beginning of cephalgia in common migraine. Alternatively or additionally, surface or depth electrodes may be implanted to measure EEG activity, and to activate the neurostimulator upon sensing the onset of an episode of migraine, such as paroxysmal activity In any case, it is desired to prevent the migraine from proceeding to its acute phase, because it is easier and more effective to control the disorder before the condition fully develops. Yet another detection strategy, which is less important but may possibly be effective in certain cases, is to use circadian or other programming to automatically activate the stimulus generator to reduce or eliminate abnormal sleep patterns upon detection thereof by monitoring REM (rapid eye movement) activity. Each of these detection strategies is effective to initiate the stimulation strategy, by which an electrical signal is generated appropriate for application to the patient's vagus nerve to modulate the activity of the brain structures including limbic system, reticular formation and hippocampus. For example, if epileptiform is being treated the modulation is effected to desynchronize the synchronous paroxysmal activity, and increase the background desynchronous activity.

According to a feature of the invention, EEG frequency spectral analysis circuitry is preferably employed to detect paroxysms in the EEG waveform sensed by the surface or depth electrodes of the automatic detection circuitry.

Broadly, then, the present invention is directed to apparatus and methods which employ a neurostimulator device, preferably implantable, for therapy or treatment of migraine or migraine episodes through nerve stimulation. The modulating signals applied to the vagus nerve may stimulate or inhibit other neural signals to produce excitatory or inhibitory neurotransmitter release, but for purposes of this disclosure both situations are included within the term "stimulating". It should be emphasized that although the preferred nerve site for application of the modulating signals is the vagus nerve, effective treatment may be achieved through application of the stimulus to one or more other nerves, particularly among the cranial nerves, and such treatment is deemed to be within the ambit of the present invention.

Accordingly, it is a more specific object of the invention to provide methods and apparatus for treating and controlling migraine by applying electrical stimuli to the patient's vagus nerve or other cranial nerve, to activate a specific group of fibers from among all of the fiber groups of the selected nerve(s), and to selectively desynchronize or possibly synchronize the patient's EEG according to the particular patient being treated and the specific nature of the migraine.

Another object of the invention is to provide methods and apparatus for treating and controlling migraine by sensing a symptom of the disorder or the occurrence of a predetermined detectable event and thereafter automatically or manually effecting modulation of vagal activity through the application of preselected stimuli to the patient's vagus nerve.

According to another important feature of the invention, a power down circuit is used in the neurostimulator device which is employed to generate the stimulating signal for modulating the vagal activity of the patient This is particularly important where the device is implanted in the patient. The frequency of migraine episodes is relatively low for most patients, which makes it possible to conserve considerable battery power between these episodes by shutting the device down into a sleep state. It is anticipated that the power drain in the power down phase will be on the order of only a few nanoamperes. The device activation time is likely to run from about 24 to about 48 hours for controlling migraine attacks, and the interval between attacks may range from several weeks to even several months. Hence, the average power consumed by the device can be reduced, through power down, to such an extent that the size of the battery may be quite small. Since battery size is by far the principal determinant of overall implanted device size, the latter can be produced in a correspondingly small package.

Projections indicate that by implementing a power down mode, the device may be produced with a weight of less than 25 grams and a battery lifetime in excess of 15 years. This means that the implanted device would normally need replacement only after a lengthy interval (similar to battery lifetime, but with an appropriate safety factor), with a concomitant reduction in the number of required surgeries. Such a device is quite cost effective. The small size of the device would also be significant from a purely cosmetic standpoint. The implanted device would be virtually unnoticeable beneath the skin, a desirable attribute for all patients and particularly young patients.

Therefore, still another object of the invention is to provide an implantable device for treating and controlling migraine by automatic or manual activation to modulate vagal activity through the application of preselected stimuli to the patient's vagus nerve, the device being automatically powered down after successful treatment or control of a migraine episode so as to conserve battery power until the next episode occurs.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which:

FIG. 2 is a simplified fragmentary illustration of a preferred embodiment of the stimulus generator and lead/electrode system of the neurostimulator implanted in the patient's body;

FIG. 3 is a detailed fragmentary illustration of the nerve electrode as implanted on the vagal nerve in the neck of the patient for modulating vagal activity;

DESCRIPTION OF THE PRESENTLY PREFERRED EMBODIMENT AND METHOD

Figure 1:
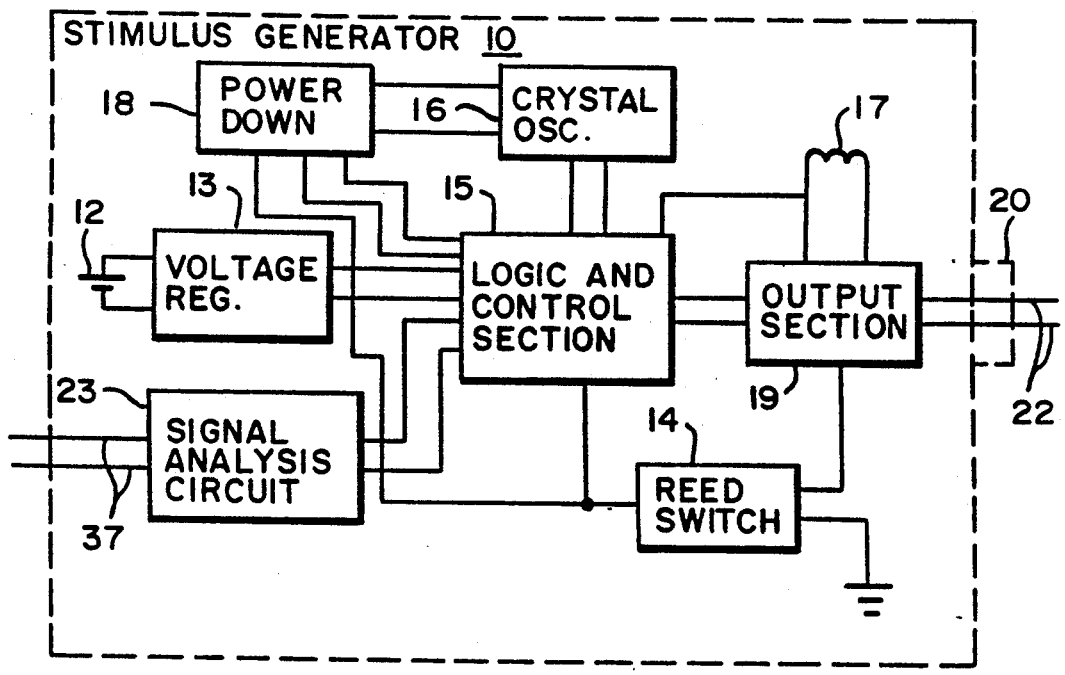
FIG. 1 is a simplified block diagram of an implantable neurostimulator electronics package (stimulus generator) for use (with appropriate parameter settings and ranges) in treating migraine according to the present invention.

Referring now to the drawings, a block diagram of the basic components of the stimulus generator of a neurostimulator and their interrelationship is illustrated in FIG. 1, and further details of location of an implantable version of the device and the associated lead/electrode system are shown in FIGS. 2 and 3. A generally suitable form of neurostimulator for use in the apparatus of the present invention is disclosed in copending U.S. patent application Ser. No. 07/434,985, filed Nov. 10, 1989, now in the names of Anthony J. Varrichio, et al. (referred to herein as "the '895 application"), assigned to the same assignee as the instant application, with modifications and additions as will be described herein. The specification of the '985 application is incorporated herein in its entirety by reference, but certain portions of it are summarized in this application for the sake of convenience to the reader.

The neurostimulator utilizes a conventional microprocessor and other standard electrical and electronic components, and in the case of an implanted device, communicates with and programmer and/or monitor located external to the patient's body by asynchronous serial communication for controlling or indicating states of the device Passwords, handshakes a parity checks are employed for data integrity. The neurostimulator also includes means for conserving energy, which is important in any battery operated device and especially so where the device is implanted for medical treatment of a disorder, and means for providing various safety functions such as preventing accidental reset of the device.

The stimulus generator 10 (FIG. is preferably adapted to be implantable in the patient's body, in a pocket formed by the surgeon just below the skin in the chest as shown in FIG. 2, although a primarily external neurostimulator may alternatively be employed The neurostimulator also includes implantable stimulating electrodes (described below) together with a lead system 22 for applying the output signal of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand and the computer. The external components of the system are not shown in the drawings.

In conjunction with its microprocessor-based logic and control circuitry, the stimulus generator 10 or other implanted or external circuitry may include detection circuitry for sensing an event indicative of onset of the migraine attack to trigger automatic delivery of the stimulating signal. For example, surface or depth electrodes may be implanted to sense specific characteristics of the patient's EEG for triggering the therapy, as will be discussed presently in conjunction with the description of FIGS. 2 and 5. Although this involves delicate electrode/lead implantation procedures as well as the requirement of circuitry for spectral analysis and/or programmable spectral or pattern recognition, it is presently believed to be the most suitable technique for detection of onset of migraine, apart from the patient's own ability to sense onset. The stimulus generator is designed, implemented and programmed to deliver a selectively patterned stimulating signal to modulate the electrical activity of the vagus nerve in a manner designed to treat and control the migraine episode.

As shown in FIG. 1, stimulus generator 10 includes a battery (or set of batteries) 12, which may be Of any reliable long-lasting type conventionally employed for powering implantable medical electronic devices (such as batteries employed in implantable cardiac pacemakers or defibrillators). In the preferred embodiment of the stimulus generator, the battery is a single lithium thionyl chloride cell The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device Among these programmable functions are output current or voltage, output signal frequency, output signal pulse width, output signal on-time, output signal off-time, daily treatment time for continuous or periodic modulation of vagal activity, and output signal-startdelay time. Such programmability allows the output signal to be selectively crafted for application to the stimulating electrode set (FIGS. 2 and 3) to obtain the desired modulation of vagal activity for treatment and control of migraine. Timing signals for the logic and control functions of the generator are provided by a crystal oscillator 16. A magnetically-actuated reed switch 14 is incorporated in the electronics package to provide the generator with the capability for patient activation thereof (by use of an external magnet, not shown, placed immediately adjacent to the package or its implant site).

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

A power down circuit 18 is electrically connected to reed switch 14, logic/control circuit 15 and crystal oscillator 16. The power down circuit is timed by the clock pulses from the crystal oscillator to reduce power to the microprocessor of section 15 and/or to the oscillator to a point at which the device is essentially in a sleep state but sufficiently alert to be awakened on command. In the preferred embodiment, power down circuit 18 initiates the power down mode or sleep state automatically, within 48 hours after the device has been activated to generate its programmed stimulating output signal. It is anticipated that a 48-hour period will be sufficient time in which to control most migraine attacks, but the period may be longer or shorter depending on the needs of the particular patient. Thereafter, the device remains in the reduced power state until the power down circuit is disabled to wake the microprocessor and/or oscillator by either manual activation of the device (for example, application of a magnet in the immediate vicinity of the reed switch) or by automatic activation upon sensing the onset of a migraine episode. Power down circuits fabricated in CMOS semiconductor circuitry are well known in the integrated circuit field, and such a circuit is readily implemented in the neurostimulator device by persons of ordinary skill in the art.

The reduced power requirement of the device in the interval between migraine episodes assures the availability of sufficient battery power to enable treatment over a much longer period than would otherwise be the case. The result is a significantly increased device lifetime, a substantially increased interval between surgical replacements of the device, and a considerable reduction in device size compared to a device without the power down feature.

Logic and control section 15 of the stimulus generator 10 controls an output circuit or section 19 which generates the programmed signal levels appropriate to the nature of the migraine episode being treated. The output section and its programmed output signal are coupled (directly, capacitively, or inductively) to an electrical connector 20 on the housing 21 of the generator and to lead assembly 22 connected to the stimulating electrodes (FIGS. 2 and 3). If EEG sensing electrodes (or eye movement sensing electrodes for REM detection) are to be implanted in the patient for triggering delivery of therapy by the stimulus generator on detection of onset of migraine, a sense signal analysis circuit 223 is provided within the generator housing 21, with connections to the microprocessor in logic and control section 15 and to the sensing electrodes. An exemplary sense signal analysis circuit for EEG activity will be described presently. The parameters of the stimulating signal of the implanted device may be calibrated by telemetry (via the programming wand) according to the needs of the particular patient and the results then programmed into the microprocessor for delivery of the appropriate treatment upon activation of the generator.

Housing 21 in which stimulus generator 10 is encased is hermetically sealed and composed of a material such as titanium which is biologically compatible with the fluids and tissue of the patient's body. Further details of suitable structure and operation of the neurostimulator, beyond those by which the device is adapted to treat migraine as described herein, are available in the '985 application, to which the reader is referred.

FIG. 2 illustrates the preferred location of implanted generator 10, in case 21 with connector 20, in the patient's chest in a cavity formed by the implanting surgeon just below the skin, much as a pacemaker pulse generator would be implanted. A stimulating nerve electrode set 25 (FIG. 3) is conductively connected to the distal end of insulated electrically conductive lead assembly 22 which is attached at its proximal end to connector 20. Electrode set 25 is a bipolar stimulating electrode, preferably of the type described in U.S. Pat. No. 4,573,481 issued Mar. 4, 1986 to Bullara. The electrode assembly is surgically implanted on the vagus nerve 27 in the patient's neck. The two electrodes 25-1 and 25-2 are wrapped about the vagus nerve, and the assembly is secured to the nerve by a spiral anchoring tether 28 preferably as disclosed in U.S. Pat. No. 4,979,511 issued Dec. 25, 1990 to Reese S. Terry, Jr. and assigned to the same assignee as the instant application. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

Depth EEG sense electrodes 36 may be implanted in spaced apart relation through the skull, and connected to leads 37 implanted via a catheter or other suitable means (not shown) and extending along the scalp and temple and then along the jawline through the neck and chest tissue to the sense signal analysis circuit 23 of stimulus generator 10. Alternatively, or additionally, if prescribed by the attending physician, eye movement sensing electrodes 33 may be implanted at or near the outer periphery of each eye socket in a suitable location to sense muscle movement or actual eye movement, as shown in FIG. 2. The sense electrodes 33, which are utilized to detect REM in a pattern indicative of the onset of migraine, particularly during patient sleep, are electrically connected to leads 34 implanted and extending toward the ears and then generally along the same path and in the same manner as described above for the EEG sense electrode leads.

The stimulus generator may be programmed with an IBM-compatible personal computer (not shown) using programming software of the type copyrighted by the assignee of the instant application with the Register of Copyrights, Library of Congress, or other suitable software based on the description herein, and a programming wand (not shown) The wand and software permit noninvasive communication with the generator after the latter is implanted. The wand is preferably powered by internal batteries, and provided with a "power on" light to indicate sufficient power for communication Another indicator light is preferably provided to show that data transmission is occurring between the wand and the generator.

Figure 4:
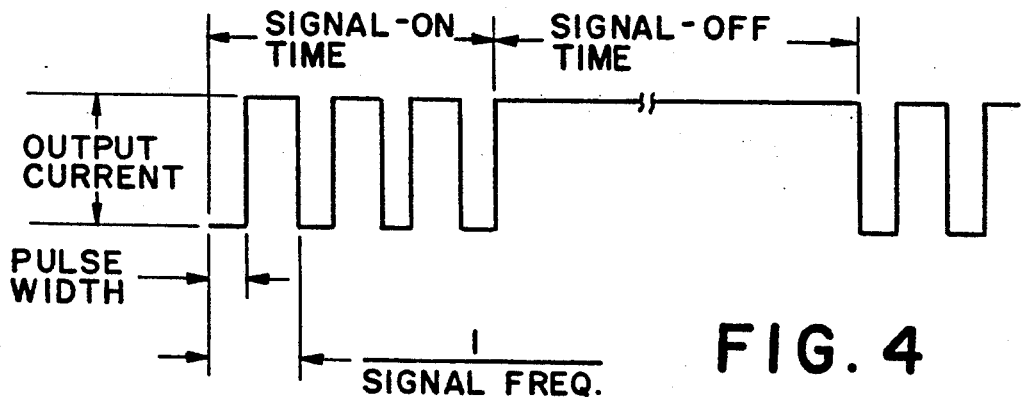
FIG. 4 is an illustrative idealized electrical output signal waveform of the stimulus generator useful for clarifying relevant parameters of the signal developed by the stimulus generator for application to the nerve.

The operation of stimulus generator 10 to control and treat migraine will be described with reference to FIG. 4, which illustrates the general nature, in idealized representation, of the output signal waveform delivered by output section 19 of the neurostimulator to electrode assembly 25. This illustration is presented principally for the sake of clarifying terminology, including the parameters of output signal on-time, output signal off-time, output signal frequency, output signal pulse width, and output signal current.

In the treatment of migraine according to the invention, the preferred stimulation strategy is to program the neurostimulator to desynchronize, or in some instances to synchronize, the patient's EEG. The decision is based upon the abnormal EEG pattern typically observed by the attending physician for the particular patient at onset and/or during the episode, and the need to correct that pattern. In the large majority of the migraine patient population, the EEG exhibits paroxysmal activity and, hence, there is a need to desynchronize. To desynchronize the EEG, the stimulus signal parameters of the pulse waveform may be programmed, for example, at a frequency of 20 Hz, output current of 1.5 mA and pulse width of 0.5 ms. Other patients may suffer excessive low voltage, fast wave activity, and for them the stimulation strategy is to modulate vagal activity in a way to synchronize the EEG. To synchronize, an exemplary pulse waveform would have corresponding parameters of 90 Hz, 1 mA, and 0.1 ms. A patient suffering from classical migraine can easily recognize the visual phenomena constituting the aura indicative of onset of the migraine attack, and consequently the preferred detection strategy is for patient activation of the neurostimulator at that time This may be accomplished in a number of different ways, one example being by placement of an external magnet directly over the location of the implanted stimulus generator to actuate reed switch 14 (FIG. 1).

A suitable range of stimulation parameters for desynchronization or synchronization of the patient's EEG activity depending on the needs of the individual patient, and the typical value of each parameter of the stimulating output signal for treatment of the migraine, are as follows:

|  | Range | Desynch, Typical | Synch, Typical |
| --- | --- | --- | --- |
| Pulse Width | 0.05-1.5 ms | 0.5 ms | 0.1 ms |
| Output Current | 0.1-5.0 mA | 1.5 mA | 1.5 mA |
| Frequency | 5-150 Hz | 25 Hz | 80 Hz |
| ON Time | 5-5000 sec | 300 sec | 30 sec |
| OFF Time | 5-5000 sec | 10 sec | 5 sec |
| Frequency sweep | 10-50 Hz | Optional | |
| Random frequency | 10-50 Hz | Optional | |

Circadian or other periodic programming may be employed in some cases, in conjunction with monitoring abnormal sleep patterns in a patient. In these cases, REM activity is increased by stimulation at the high frequencies (e.g., 80 Hz) for increased synchronization of the EEG.

Figure 5:
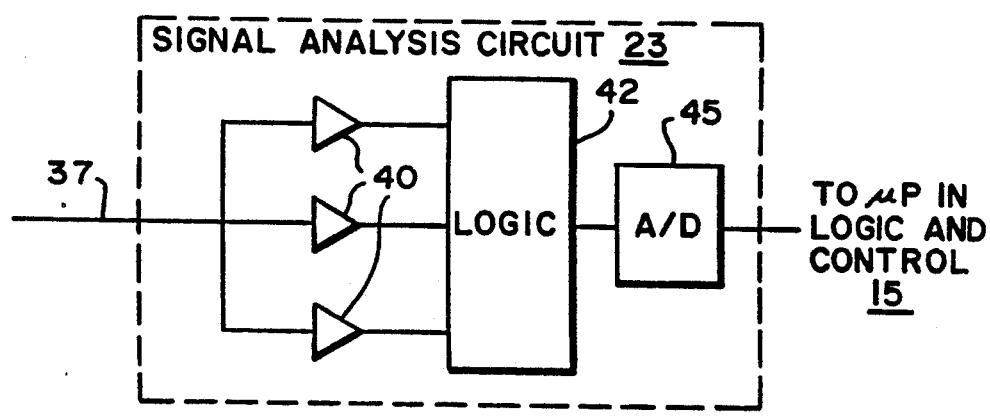
FIG. 5 is a simplified block diagram of an EEG spectral analysis circuit used in the stimulus generator.

If sense electrodes are implanted to detect onset of migraine, a signal analysis circuit 23 is incorporated in the stimulus generator 10 (FIG. 1). Referring to FIG. 5, where the sense electrodes are EEG electrodes such as 36 and associated leads 37 of FIG. 2, analysis circuit 23 is implemented for EEG detection and analysis To that end, circuit 23 includes a plurality of parallel active sense signal bandpass filters 40 staged to provide selective filtering in the ranges from 0-2 Hz, 2-4 Hz and 15-20 Hz, for example; a logic circuit 42 to select the output of one filter from among the plurality of filters 40; and an analog/digital (A/D) converter 45. The outputs of the filters are individually sampled by the logic circuit 42, and the sampling rate, averaging time interval, and weighting assigned to each sense signal band, are controlled by the microprocessor in the logic and control section 15 of the stimulus generator 10 (FIG. 1), to detect the EEG pattern. Upon detection of EEG changes symptomatic of the onset of an episode of migraine specific to the individual patient, the processed digital signal is supplied to the microprocessor to trigger application of the stimulating signal to the patient's vagus nerve.

Various features may be incorporated into the neurostimulator for purposes of the safety and comfort of the patient. For example, comfort would be enhanced by programming the output stimulus to ramp up during the first two seconds of stimulation, rather than to be delivered abruptly. Also, the implanted generator may be provided with a clamping circuit to limit the maximum voltage, to 14 volts for example, which is delivered to the vagus nerve. Such a maximum limit is designed to prevent injury to the patient's vagus nerve.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and messages to facilitate simple and rapid programming while keeping the user fully informed of everything occurring at each step of a sequence Programming capabilities should include capability to modify the adjustable parameters of the stimulus generator and its output signal, to test device diagnostics, and to store and retrieve telemetered data. It is desirable that when the implanted unit is interrogated, the present state of the adjustable parameters is displayed on the monitor of external PC so that the programmer may then conveniently change any or all of those parameters at the same time; and, if a particular parameter is selected for change, all permissible values for that parameter are displayed so that the programmer may select an appropriate desired value for entry into the neurostimulator.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. The nerve electrodes are capable of indefinite use absent indication of a problem with them observed on the diagnostics testing.

Although a preferred embodiment and methods of treating and controlling migraine according to the invention have been described herein, it will be apparent to those skilled in the field from a consideration of the foregoing description that variations and modifications of such embodiments, methods and techniques may be made without departing from the true spirit and scope of the invention. For example, although a totally implantable device is preferred, the electronic energization package may, if desired, be primarily external to the body. Stimulation can be achieved with an RF power device implemented to provide the necessary energy level. The implanted components may be limited to the lead/electrode assembly, a coil and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes. The disadvantages of such an implementation are that the external transmitter must be carried by the patient, greater power is required for activation, and the output current to the nerve is less stable.

An external stimulus generator may be employed with leads extending percutaneously to the implanted nerve electrode set. The major problem encountered with this technique is the potential for infection, but it is useful to allow short term testing of the patient to determine whether migraine suffered by the patient under observation is amenable to successful treatment. If it is, a more permanent implant may be provided Accordingly, it is intended that the invention shall be limited only to the extent required by the appended claims and the rules and principles of applicable law.

What is claimed is:

1. A therapeutic method of treating symptoms of migraine in patients experiencing migraine attacks, which includes the steps of:
   detecting a physiological symptom associated with onset of a migraine attack in a patient under treatment, and
   in response to detection of such symptom, selectively applying a programmed electrical stimulus to the patient's vagus nerve for modulating the electrical activity of preselected fibers of the vagus nerve in a manner to alleviate the migraine attack.

2. The method of claim 1, wherein:
   the detected symptom is paroxysmal activity of the patient's EEG, the predetermined electrical stimulus is a signal in the form of a pulse waveform having a plurality of programmable signal parameters, and the method further includes
   programming at least some of the signal parameters of the pulse waveform to modulate the vagus nerve electrical activity in a manner to desynchronize the patient's EEG upon detection of such EEG paroxysmal activity.

3. The method of claim 1, wherein:
   the detected symptom is excessive low voltage, fast wave activity of the patient's EEG, the predetermined electrical stimulus is a signal in the form of a pulse waveform having a plurality of programmable signal parameters, and the method further includes
   programming at least some of the signal parameters of the pulse waveform to modulate the vagus nerve electrical activity in a manner to synchronize the patient's EEG upon detection of such low voltage, fast wave activity of the EEG.

4. The method of claim 1, wherein:
   the detecting of such symptom is performed by detecting one of (i) a visual pattern constituting an aura perceived by the patient, (ii) abnormal EEG waves over the central temporal region of the patient, and (iii) abnormal sleep patterns of the patient, associated with onset of a migraine attack.

5. The method of claim 1, wherein:
   the symptom is a subjective indication perceived by the patient as being associated with the onset of an episode of migraine, and
   the selective application of the stimulus is performed by the patient manually initiating such application upon perceiving such subjective indication.

6. The method of claim 5, wherein the electrical stimulus is a pulse waveform, and including:
   programming parameters of the pulse waveform including pulse width, output current, output voltage, frequency and on and off times as prescribed to treat the migraine of the particular patient, prior to applying the pulse waveform to the patient's vagus nerve.

7. The method of claim 1, wherein:
   the electrical stimulus is applied to the patient's vagus nerve by application at a site on the vagus nerve in the patient's neck.

8. The method of claim 1, wherein:
   the electrical stimulus is a pulse waveform having parameter values including pulse width, output current or output voltage, frequency, on time and off time, which are selectively programmable, and
   the electrical stimulus is programmed by programming at least some of said parameter values prior to applying the stimulus to the patient's vagus nerve.

9. A method of treating patients suffering from migraine episodes, which includes the steps of:
   providing an electrical stimulus generator with an electrical output signal having parameters which are programmable within respective ranges predetermined, when the programmed output signal is properly applied to the vagus nerve of the patient, to relieve symptoms of migraine, and adapting the stimulus generator to generate its output signal upon selective activation of the stimulus generator,
   implanting the stimulus generator in the patient's body, and implanting a nerve electrode to receive the output signal of the stimulus generator on the vagus nerve of the patient, and
   programming at least some of the programmable parameters of the output signal of the stimulus generator according to the nature of the migraine suffered by the particular patient under treatment to modulate the electrical activity of the vagus nerve in a predetermined manner, upon activation of the stimulus generator and consequent application of the programmed output signal thereof to the vagus nerve through the nerve electrode implanted thereon, to alleviate symptoms of a migraine episode experienced by the patient.

10. The method of claim 9, wherein:
    the output signal of the stimulus generator is a pulse waveform and the programmable parameters thereof include pulse width, output current or output voltage, frequency, on time and off time, and
    the implanting of the nerve electrode is performed by securing the electrode to the vagus verve at a site in the patient's neck and electrically connecting the electrode via a conductive lead to the stimulus generator.

11. The method of claim 9, wherein:
    the adapting of the stimulus generator to generate its output signal upon selective activation is performed by providing the stimulus generator with a sensor to detect a symptom associated with onset of a migraine episode and to activate the stimulus generator upon such detection, and including
    implanting the sensor together with the stimulus generator.

12. The method of claim 9, further including:
    deactivating the output signal of the stimulus generator after a predetermined time interval of activation thereof, to conserve power in the stimulus generator.

13. Apparatus for therapy of patients suffering from migraine by treating symptoms of the migraine associated, in some patients, with a synchronized EEG and, in other patients, with a desynchronized EEG, in which the apparatus includes an implantable programmable neurostimulator device adapted to generate a programmed electrical output signal upon activation of the device, and an implantable electrical lead assembly connectable at its proximal end to the neurostimulator device to receive the programmed output signal thereof and having an electrode at its distal end adapted to be secured to the patient's vagus nerve for electrical excitation of the nerve to modulate the electrical activity of the nerve, characterized in that the apparatus further includes:

sensor means electrically coupled to the neurostimulator device for detecting the occurrence of a predetermined symptom of the migraine, activator means responsive to detection of such occurrence for activating the neurostimulator device to apply its programmed electrical output signal to the electrical lead assembly, the neurostimulator device including means for rendering the output signal parameters thereof programmable only within respective ranges preselected for desynchronizing or synchronizing the patient's EEG according to the specific nature of the migraine suffered by the particular patient under treatment, whereby when the output signal is so programmed and the activator means detects the occurrence of the predetermined symptom of the migraine, the electrical activity of the vagus nerve is modulated to desynchronize or synchronize the patient's EEG according to the selected programming so as to relieve the detected symptom of the migraine.

14. The apparatus of claim 13, wherein said neurostimulator device further includes:

power down means for reducing the power consumption of the neurostimulator device between episodes of migraine.

15. The apparatus of claim 13, in which:

the neurostimulator device further includes manual activation means for alternative patient activation of the neurostimulator device to cause generation of the programmed electrical output signal thereof.

16. The apparatus of claim 15, wherein said neurostimulator device includes:

power conservation means responsive to the passage of a predetermined time interval following activation of the neurostimulator device for deactivation thereof to power the neurostimulator device down until subsequent activation thereof by the activator means or the manual activation means.

17. The apparatus of claim 13, in which:

the neurostimulator device further includes analyzer means for assisting in the determination that a symptom of migraine is occurring.

18. The apparatus of claim 13, in which the neurostimulator device includes:

means for generating the electrical output signal of the device in the form of a pulse waveform, and selection means for programming signal parameters of the pulse waveform, including width of pulses, output current, output voltage, pulse frequency, and on time and off time of the waveform.

* * * * *